US008535731B2

(12) United States Patent
Danoux et al.

(10) Patent No.: US 8,535,731 B2
(45) Date of Patent: Sep. 17, 2013

(54) **USE OF EXTRACTS OF THE *CASSIA ALATA* PLANT**

(75) Inventors: Louis Danoux, Saulxures les Nancy (FR); Gilles Pauly, Nancy (FR); Phillippe Moser, Essey-les-Nancy (FR)

(73) Assignee: BASF Beauty Care Solutions France S.A.S., Lyons (FR)

( * ) Notice: Subject to any disclaimer, the term of this patent is extended or adjusted under 35 U.S.C. 154(b) by 930 days.

(21) Appl. No.: 10/362,859

(22) PCT Filed: Aug. 21, 2001

(86) PCT No.: PCT/EP01/09602
§ 371 (c)(1),
(2), (4) Date: Feb. 26, 2003

(87) PCT Pub. No.: WO02/17938
PCT Pub. Date: Mar. 7, 2002

(65) Prior Publication Data
US 2003/0180231 A1 Sep. 25, 2003

(30) Foreign Application Priority Data
Aug. 29, 2000 (FR) ..................................... 00 11040

(51) Int. Cl.
*A61K 36/482* (2006.01)
*A61K 8/00* (2006.01)

(52) U.S. Cl.
USPC .......................................... 424/725; 424/401

(58) Field of Classification Search
USPC ................................ 424/725, 401
See application file for complete search history.

(56) References Cited

U.S. PATENT DOCUMENTS

| 4,172,887 A | 10/1979 | Vanlerberghe et al. | |
| 4,710,495 A * | 12/1987 | Bodor | ............................ 514/174 |
| 5,466,455 A | 11/1995 | Huffstutler, Jr. et al. | |
| 5,705,169 A | 1/1998 | Stein et al. | |
| 5,730,960 A | 3/1998 | Stein et al. | |
| 5,945,091 A | 8/1999 | Habeck et al. | |
| 6,193,960 B1 | 2/2001 | Metzger et al. | |
| 6,709,664 B2 * | 3/2004 | Resnick | ......................... 424/401 |

FOREIGN PATENT DOCUMENTS

| DE | 1 165 574 A | 3/1964 |
| DE | 2 024 051 A | 12/1971 |
| DE | 197 12 033 A1 | 9/1998 |
| DE | 197 56 377 A1 | 6/1999 |
| EP | 0 693 471 B1 | 1/1996 |
| EP | 0 694 521 B1 | 1/1996 |
| EP | 0 818 450 B1 | 1/1998 |
| FR | 2 252 840 A | 8/1975 |
| GB | 962919 A | 7/1964 |
| GB | 1 333 475 A | 10/1973 |
| JP | 04 338313 A | 11/1992 |
| JP | 07 165527 A | 6/1995 |
| JP | 07-278003 A | 10/1995 |
| JP | 10 008049 A | 1/1998 |
| JP | 11-106336 A | 4/1999 |
| JP | 2000-178199 A | 6/2000 |
| JP | 2001 039823 A | 2/2001 |
| JP | 2001039823 | 2/2001 |
| JP | 2001 081021 A | 3/2001 |
| JP | 2001081021 | 3/2001 |

OTHER PUBLICATIONS

Benjamin, T. et al., Investigation of Cassia alata, a Plant Used in Nigeria in the Treatment of Skin Disease, Quart. J. Crude Drug Res. 19 (1981), No. 2-3, pp. 93-96.*
Smith, R. et al., Anthraquinones from the leaves of Cassia alata from Fiji, New Zealand J. of Science, 1979, vol. 22, 123-5.*
Osumi, K., Cosmetic JP404338313A, Nov. 25, 1992, abstract.*
Wrinkles and Wrinkle Treatments, (http://www.skin-care-reviews.com/wrinkle-treatments.html), p. 1-6, printed on Feb. 15, 2007.*
Nonogawa Shoji KK., "Cosmetic", JP 04-338313 A, Nov. 25, 1992, English translation (PTO 06-4920).*
Poucher's Perfumes, Cosmetics and Soaps, 2000, (10$^{th}$ ed. by Hilda Butler), Kluwer Academic Publishers, pp. 403-405.*
Database Biosis 'Online! Biosciences Information Service, Philadelphia, PA, US; Database accession No. PREV198069073723 XP002172488 abstract & R.M. Smith et al.: "Anthraquinones from the leaves of cassia alata from fiji" New Zealand Journal of Science, vol. 22,—1979 pp. 123-126, abstract.
Database Biosis 'Online! Biosciences Information Service, Philadelphia, PA, US; Database accession No. PREV198273044797 XP002172489 abstract & T.V. Benjamin et al.: "Investigation of cassia alata a plant used in nigeria in the treatment of skin diseases" Quarterly Journal of Crude Drug Research, vol. 19,—1996, pp. 93-96.
Database Biosis 'Online! Biosciences Information Service, Philadelphia, PA, US; Database accession No. PREV1999192079912 XP002172490 abstract & S. Palanichamy et al.: "wound healing activity of cassia alata" FITOTERAPIA, vol. 62,—1991, pp. 153-156.
Palanichamy et al., "Analgesic Activity of Cassia Alata Leaf Extract and Kaempferol 3-O-Sophoroside", Journal of Ethnopharmacology, 29, Elsevier Scientific Publishers Ireland Ltd., (1990), pp. 73-78.
Palanichamy et al., "Antibacterial Activity of Cassia Alata", FITOTERAPIA, vol. LXII, No. 3, (1991), pp. 249-252.
Ibrahim et al., "Antimicrobial activity of Cassia Alata from Malaysia", Journal of Ethnopharmacology, 45, (1995), pp. 151-156.
Bruchhausen, Hagers Handbuch der pharmazeutischen Praxis, 5$^{th}$ Edition, vol. 2, Springer Verlag, Berlin-Heidelberg-New York, (1991), pp. 1026-1030.
Finkel, "Formulierung kosmetischer Sonnenschutzmittel", SÖFW-Journal, 122, (1996), pp. 543-546 & 548.
Finkel, "Formulierung kosmetischer Sonnenschutzmittel", Parfumerie und Kosmetik, 80, No. 3, (1999), pp. 10-12, 14-15.

(Continued)

*Primary Examiner* — Gina C Justice
(74) *Attorney, Agent, or Firm* — Servilla Whitney LLC

(57) ABSTRACT

Extracts of the plant *Cassia alata* are used in cosmetic and/or dermatological skin care preparations. These preparations possess antioxidative and anti-inflammatory properties and exhibit preventive and curative effect on skin aging.

15 Claims, No Drawings

(56) References Cited

OTHER PUBLICATIONS

Hissin et al., "A Fluorometric Method for Determination of Oxidized and Reduced Glutathione in Tissues", Analytical Biochemistry, 74, (1976), pp. 214-226.

Falbe, "Surfactants in Consumer Products", Springer Verlag, Berlin, (1987), pp. 54-124.

Falbe, "Katalysatoren, Tenside und Mineralöladditive" (Catalysts, Surfactants and Mineral Oil Additives), Thieme Verlag, Stuttgart, (1978), pp. 123-217.

Todd et al., "Volatile silicone fluids for cosmetic formulations", Cosmetics and Toiletries, vol. 91, (Jan. 1976), pp. 29-32.

Lochhead et al., "Encyclopedia of Polymers and Thickeners for Cosmetics", Cosmetics & Toiletries, vol. 108, (May 1993), pp. 95-114, 116-124, 127-130, 132-135.

"Kosmetische Färbemittel", Farbstoffkommission der Deutschen Forschungsgemeinschaft, Verlag Chemie, Weinheim, (1984), pp. 81-106.

Paul (Editor), Cell and Tissue Culture, Churchill Livingstone, 5th Edition, (1975), pp. 219-231.

Mowry, "The Special Value of Methods That Color Both Acidic and Vicinal Hydroxyl Groups in the Histochemical Study of Mucins", Annals New York Academy of Sciences, 106, Art. 2, (1963), pp. 402-406.

Begum, et al., "Ethnobotanical Review of Medicinal Plants Used for Skin Diseases and Related Problems in Northeastern India", Journal of Herbs, Spices & Medicinal Plants, vol. 7 (3), The Haworth Press, Inc., (2000), pp. 55-93.

Ohsumi, et al., "Anti-Inflammatory Activities of Some Traditional Indonesian Crude Drugs", Natural Medicines, 49 (4), (1995), pp. 472-474.

Contet-Audonneau, J.L. et al., "A Histological Study of Human Wrinkle Structures: Comparison Between Sun-Exposed Areas of the Face, With or Without Wrinkles, and Sun-Protected Areas", *British Journal of Dermatology 1999*;140 Dec. 12, 1998 , 1038-1047.

Bianchi, Luca et al., "Abnormal Bcl-2 and "Tissue" Transglutaminase Expression in Psoriatic Skin", *J. Invest. Dermatol. 103*, 1994, 829-833.

Botchkareva, Natalia et al., "Apoptosis in the Hair Follicle", *Journal of Investigative Dermatology*, vol. 126 2006, 258-264.

Darby, IA et al., "Apoptosis is increased in a model of diabetes-impaired wound healing in genetically diabetic mice", *Int. J Biochem Cell Biol.*: 29: 191-200, Jan. 1997, (Abstract).

Raj, Deepak et al., "Keratinocyte Apoptosis in Epidermal Development and Disease", *J Invest Dermatol.: 126*(2) Feb. 2006, 243-257.

\* cited by examiner

USE OF EXTRACTS OF THE *CASSIA ALATA* PLANT

BACKGROUND OF THE INVENTION

This invention relates generally to care products and, more particularly, to the use of plant extracts of the plant *Cassia alata* in cosmetic and dermatological preparations.

PRIOR ART

Today, cosmetic preparations are available to the consumer in a variety of combinations. Consumers not only expect these cosmetics to have a certain care effect or to eliminate a certain deficiency, they are also increasingly demanding products which combine several properties and thus show an improved performance spectrum. Consumers are also entitled to expect the composition of the product to have optimal dermatological compatibility so that even consumers with sensitive skin do not react with irritation. In addition, the preparations are also expected to perform other functions which are related increasingly to care and particularly protection. There is a particular interest in substances which represent active principles that impart, for example, caring, anti-ageing and revitalizing properties to the skin and, at the same time, positively influence, or at least do not adversely affect, the technical properties of the cosmetic product, such as storage stability, light stability and formulatability. In addition, consumers demand high dermatological compatibility and, above all, the use of natural products. Also, it is desirable to obtain distinctly better products by combining already known active principles or by discovering new applications for already known classes of substances. However, one disadvantage in this regard is often that a combination of active principles is only obtained when different plant extracts are simultaneously used in different quantity ratios.

Extracts of plants and their ingredients are being increasingly used in cosmetic and dermatological products. For many years, plant extracts have been used for medicinal purposes and also for cosmetic purposes in many different cultures. These plant extracts were often known only for very specific individual effects which limited their scope of application.

DESCRIPTION OF THE INVENTION

The problem addressed by the present invention was to provide extracts of renewable raw materials for cosmetic and/or dermatological application which, at the same time, would lend themselves to many uses as care agents in various areas of cosmetology and/or dermatology.

Another problem addressed by the invention was to provide plant extracts of a plant for cosmetic and/or dermatological application which, besides care and protective properties, would above all have a preventive and curative effect on signs of aging of the skin and would develop reactivating and revitalizing activity.

The present invention relates to the use of extracts of the plant *Cassia alata* in cosmetic and/or dermatological skin care preparations. It has surprisingly been found that the use of extracts of *Cassia alata* leads to products which, at one and the same time, show favorable skin care and protecting properties and high dermatological compatibility. The preparations thus obtained are distinguished by particularly good skin care effects. Besides antioxidative and anti-inflammatory properties, they also have a preventive and curative effect on signs of skin again and revitalizing and reactivating activity on the skin.

These multiple applications of the preparation according to the invention from the renewable raw material of the plant *Cassia alata* make it very attractive both to the market and to the consumer. Accordingly, the complex problem addressed by the invention has been solved by the use of an extract of the plant *Cassia alata*.

In the context of the present invention, the term plant is understood to include both whole plants and plant parts (leaves, roots, flowers) and mixtures thereof.

*Cassia alata*

The extracts to be used in accordance with the invention are obtained from plants of the genus *Caesalpiniaceae*, more particularly from the relatively uncommon species *Cassia alata*. The *Cassia* species are also known collectively as winter's bark. The species *Cassia angustifolia*, *Cassia acutifolia* and *Cassia senna* are common. The plant *Cassia alata* is a herbaceous, dense shrub 2 to 3 meters in height with leaves 20 to 60 cm in length. The pinnate, alternate leaves number 8 to 14 pairs and are elongate and blunt with a length of 5 to 15 cm and a width of 3 to 8 cm. The flowers appear on short stems and the buds are enclosed in yellow bracts.

It is widespread in the tropics and extends from tropical regions of America through Africa, India, Indonesia and Malaysia. The plant to be used in accordance with the invention may originate from any of the regions mentioned.

In traditional Indian medicine, this plant has already been used for the treatment of coughs and asthma. It has also been administered against snake bites. As an anti-snake bite agent, the fresh leaves are internally applied. In Malaysia, the leaves were used as a medicine against ring worm. In Indonesia, the crushed fresh leaves of *Cassia alata* are used against herpes. An article in Journal of Ethnopharmacology reports on analgesic properties of an 85% ethanol extract of defatted leaves of *Cassia alata* (cf. Palanichamy, S., Nagarajan, S.: Journal of Ethnopharmacology; 1990, 29, 73-78). In the journal Fitoterapia, the same authors describe the antibacterial activity of an 85% ethanol extract of the defatted leaves (Palanichamy, S., Amala Bhaskar, E., Nagarajan, S.: Fitoterapia, 1991, 62, 249-252). An antifungal activity of a 95% ethanol extract of the defatted leaves of *Cassia alata* against fungi of the genus Trichophyton and Microsporum was discovered by Ibrahim and Osman and reported in Journal of Ethnopharmacology (Ibrahim D., Osman, H. A.; Journal of Ethnopharmacology; 1995, 45, 151-156).

The extracts of the plant are known as medicinal active principles both in traditional medicine and in modern research. Their antimicrobial and analgesic effects have already been demonstrated.

Extraction

The extracts to be used in accordance with the invention may be prepared by known methods of extracting plants or parts thereof. Particulars of suitable conventional extraction processes, such as maceration, remaceration, digestion, agitation maceration, vortex extraction, ultrasonic extraction, countercurrent extraction, percolation, repercolation, evacolation (extraction under reduced pressure), diacolation and solid/liquid extraction under continuous reflux in a Soxhlet extractor, which are familiar to the expert and which may all be used in principle, can be found, for example, in Hagers Handbuch der pharmazeutischen Praxis (5th Edition, Vol. 2, pp. 1026-1030, Springer Verlag, Berlin-Heidelberg-New York 1991). Fresh or dried plants or parts thereof are suitable as the starting material although plants and/or plant parts which may be mechanically size-reduced and optionally defatted before extraction are normally used. Any size reduction methods known to the expert, for example comminution with a bladed tool, may be used. The leaves of the plant are particularly preferred for extraction.

Preferred solvents for the extraction process are organic solvents, water or mixtures of organic solvents and water, more particularly low molecular weight alcohols, esters, ethers, ketones or halogenated hydrocarbons with more or less large water contents (distilled or non-distilled), preferably aqueous alcoholic solutions with more or less large water contents. Extraction with water, methanol, ethanol, propanol, butanol and isomers thereof, acetone, propylene glycols, polyethylene glycols, ethyl acetate, dichloromethane, trichloromethane and mixtures thereof is particularly preferred. The extraction process is generally carried out at 20 to 100° C., preferably at 80 to 100° C. and more particularly at 80 to 90° C. In one possible embodiment, the extraction process is carried out in an inert gas atmosphere to avoid oxidation of the ingredients of the extract. The extraction times are selected by the expert in dependence upon the starting material, the extraction process, the extraction temperature and the ratio of solvent to raw material, etc. After the extraction process, the crude extracts obtained may optionally be subjected to other typical steps, such as for example purification, concentration and/or decoloration. If desired, the extracts thus prepared may be subjected, for example, to the selective removal of individual unwanted ingredients. The extraction process may be carried out to any degree, but is usually continued to exhaustion. Typical yields (=extract dry matter, based on the quantity of raw material used) in the extraction of dried plants or dried plant parts (optionally defatted) are in the range from 10 to 20, preferably 12 to 19 and more particularly 13 to 16% by weight. The present invention includes the observation that the extraction conditions and the yields of the final extracts may be selected according to the desired application. If desired, the extracts may then be subjected, for example, to spray drying or freeze drying.

The quantity of plant extracts used in the preparations mentioned is governed by the concentration of the individual ingredients and by the way in which the extracts are used. In general, the total quantity of plant extract present in the preparations according to the invention is 0.001 to 25% by weight, preferably 0.01 to 5% by weight and more particularly 0.05 to 1.5% by weight, based on the final preparation, with the proviso that the quantities add up to 100% by weight with water and optionally other auxiliaries and additives.

The extracts according to the invention have an active substance content in the extracts of 5 to 100% by weight, preferably 10 to 95% by weight and more particularly 20 to 80% by weight. In the context of the invention, the active substance content is the sum total of all the active substances present in the extract, based on the dry weight of the extract.

Active substance in the context of the invention relates to the ingredients present in the extract even if their content and identity have yet to be established by conventional methods known to the expert. Active substances in the context of the invention are also any ingredients present in the extract of which the effect is either already known or has not yet been identified by conventional methods known to the expert.

Active substance in the context of the invention relates to the percentage content of substances and auxiliaries and additives present in the preparation except for the water additionally introduced.

The total content of auxiliaries and additives may be 1 to 50% by weight and is preferably 5 to 40% by weight, based on the final cosmetic and/or dermatological preparations. The preparations may be produced by standard cold or hot processes but are preferably produced by the phase inversion temperature method.

Extracts

The extracts of the plant *Cassia alata* according to the invention generally contain substances from the group consisting of flavone derivatives, more particularly kaempferol and kaempferol derivatives, tannins, coumarins, anthraquinones and also free phenol acids, more particularly p-hydroxybenzoic acid. The extracts differ in composition according to the starting material and extraction method selected.

Flavone derivatives in the context of the invention are understood to be those which can be isolated from the plant *Cassia alata*. More particularly, they are hydrogenation, oxidation or substitution products of 2-phenyl-4H-1-benzopyran; hydrogenation may already be present in the 2,3-position of the carbon chain, oxidation may already be present in the 4-position and substitution products are understood to be the replacement of one or more hydrogen atoms by hydroxy or methoxy groups. Accordingly, this definition also encompasses flavans, flavan-3-ols (catechols), flavan-3,4-diols (leucoanthocyanidines), flavones, flavonols and flavonones in the traditional sense. Particularly preferred flavone derivatives isolated from the plant *Cassia alata* are kaempferol and kaempferol such as, for example, kaempferol-3-O-sophoroside, kaempferol-7-rhamnoside, kaempferol-3,7-dirhamnoside.

Tannins in the context of the invention are tannins which can be isolated from the plant *Cassia alata*. More particularly, they are polyphenols which may also be referred to as gallotannins by virtue of their derivation from gallic acid. They are mixtures of substances of the pentadigalloyl glucose type (C76H52046, MR 1701,22). Tannins are also substances formed by oxidative coupling of the galloyl residues in 1,2,3,4,6-pentagalloyl-D-glucose and derivatives of such substances.

Coumarins in the context of the invention are understood to be coumarins which can be isolated from the plant *Cassia alata*. The name coumarin is a synonym and is equivalent to the names cumarin, chromen-2-one, 2H-1-benzopyran-2-one, o-coumaric acid lactone and tonka bean camphor. Coumarin is the cyclization product from coumaric acid. Coumaric acid is ortho-hydroxycinnamic acid. In the context of the invention, coumarin is also understood to include the glucoside of coumaric acid.

Anthraquinones in the context of the invention are anthraquinones which can be isolated from the plant *Cassia alata*. More particularly, they are anthraquinone or oxidation or substitution products of 9,10-anthracene dione, substitution products being understood to be the replacement of one or more hydrogen atoms by hydroxy or methyl groups. The anthraquinones are in particular alizarin, quinizarin, chrysazin, hytsazarin, purpurin, chrysophanic acid, quinalizarin and flavopurpurin.

In the context of the invention, free phenol acids are understood to be those which can be isolated from the plant *Cassia alata*, preferably p-hydroxybenzoic acid and o-hydroxybenzoic acid or salicylic acid.

Care Preparations

Care preparations in the context of the invention are understood to be skin care preparations. These care preparations have inter alia stimulating, healing and regenerating effects on the skin. Preferred care preparations in the context of the invention are those which have a stimulating effect on the skin cells and their functions and a regenerating effect on the skin and a protective effect against environmental influences on the skin. Other preferred care preparations in the context of the invention are those which can either ameliorate or cure various diseases of the skin through their various effects on the appearance and function of the skin. In principle, the extracts according to the invention may be used in any cosmetic products for topical application. Examples of cosmetic products and their formulations are described in Tables 12 to 15.

The present invention includes the observation that particularly effective cosmetic preparations are obtained through the interaction of the ingredients of the plant extracts, particularly those mentioned above.

The preparations according to the invention have an excellent skin-care effect coupled with high dermatological compatibility. In addition, they show high stability, more particularly to oxidative decomposition of the products.

In the context of the invention, the terms "preparations", "final preparations" and "agents" are synonymous with the term "care preparations".

Active substance in the context of the invention relates to the percentage content of substances and auxiliaries and additives present in the preparations except for the water additionally introduced.

The present invention also relates to the use of extracts of Cassia alata in care preparations for the preventive or healing treatment of signs of skin ageing. Another name for care preparations of this type is anti-ageing preparations. Such signs of ageing include, for example, any type of wrinkling or lining. The treatments include slowing down of the skin ageing processes. The ageing signs can have various causes. More particularly, they are caused by UV-induced skin damage. In one particular embodiment of the invention, the care preparations are used for the treatment of UV-induced ageing of the skin. In another particular embodiment, the care preparations according to the invention are used for the treatment of induced apoptosis and correspondingly induced signs of skin ageing attributable to a lack of growth factors.

In the context of the invention, apoptosis is understood to be the controlled cell death of certain unwanted or damaged cells. It is an active cell process (suicide on command). Apoptosis is initiated by oxidative stress (UV radiation, inflammation), by a deficiency of growth factors or by toxins (pollutants, genotoxins, etc.). In the skin ageing process, for example, apoptosis of the skin cells can be induced by a deficiency of growth factors in the skin. In the apoptosis-affected cells, the nuclear DNA is degraded by the specific enzyme endonuclease and the DNA fragments are channeled into the cytoplasm. In principle, growth factors are understood to be genetic or extrinsic growth factors which stimulate the growth of skin and hair cells. They include, for example, hormones and chemical mediators or signal molecules. Examples are polypeptide growth factors and glycoprotein growth factors. Mention is made here of the epidermal growth factor (EGF), which consists of 53 amino acids and hence represents a polypeptide growth factor, or fibrillin which is a glycoprotein. Other growth factors are, for example, urogastrone, laminin, follistatin and heregelin.

The present invention also relates to the use of extracts of the plant Cassia alata in sun protection compositions.

Sun (UV) Protection Factors

Sun protection factors or UV protection factors in the context of the invention are light protection factors which are useful in protecting human skin against harmful effects of direct and indirect solar radiation. The ultraviolet radiation of the sun responsible for tanning of the skin is divided into the sections UV-C (wavelengths 200-280 nm), UVB (280-315 nm) and UVA (315-400 nm).

The pigmenting of normal skin under the influence of solar radiation, i.e. the formation of melanins, is differently effected by UVB and UVA. Exposure to UVA (long-wave UV) results in darkening of the melanins already present in the epidermis without any sign of harmful effects. It is different with so-called short-wave UV (UVB). This promotes the formation of so-called late pigment through the reformation of melanins. However, before the (protective) pigment is formed, the skin is exposed to the unfiltered radiation which, depending on the exposure time, can lead to reddening of the skin (erythema), inflammation of the skin (sunburn) or even blisters.

Extracts of the plant Cassia alata are used as UV absorbers or light filters which convert UV radiation into harmless heat. They may additionally be present in combination with other sun protection factors or UV protection factors.

These other UV protection factors are, for example, organic substances (light filters) which are liquid or crystalline at room temperature and which are capable of absorbing ultraviolet radiation and of releasing the energy absorbed in the form of longer-wave radiation, for example heat. UVB filters can be oil-soluble or water-soluble. The following are examples of oil-soluble substances:

3-benzylidene camphor or 3-benzylidene norcamphor and derivatives thereof, for example 3-(4-methylbenzylidene)-camphor as described in EP-B1 0693471;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone as described in EP 0818450 A1 or Dioctyl Butamido Triazone (UVAsorb® HEB);

propane-1,3-diones such as, for example, 1-(4-tert.butylphenyl)-3-(4'-methoxyphenyl)-propane-1,3-dione;

ketotricyclo(5.2.1.0)decane derivatives as described in EP 0694521 B1.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UVA filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789) or 1-phenyl-3-(4'- isopropylphenyl)-propane-1,3-dione and the enamine compounds described in DE 197 12 033 A1 (BASF). The UVA and UVB filters may of course also be used in the form of mixtures. Particularly favorable combinations consist of the derivatives of benzoyl methane, for example 4-tert.butyl-4'-methoxydibenzoylmethane (Parsol®) 1789) and 2-cyano-3,3-phenylcinnamic acid-2-ethyl hexyl ester (Octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or dimethicones. So-called micro- or nanopigments are preferably used in sun protection products. Micronized zinc oxide is preferably used. Other suitable UV filters can be found in P. Finkel's review in SÖFW-Journal 122, 543 (1996) and in Parfümerie und Kosmetik 3 (1999), pages 11 et seq.

The present invention also relates to the use of extracts of the plant *Cassia alata* in sun protection compositions for protecting the skin cells against UV-induced DNA damage.

The present invention also relates to the use of extracts of the plant *Cassia alata* in cosmetic and/or dermatological care preparations against UV-induced skin cell damage.

UVA rays penetrate into the dermis where they lead to oxidative stress which is demonstrated by lipoperoxidation of the cytoplasm membranes. The lipoperoxides are degraded to malonaldialdehyde which will crosslink many biological molecules, such as proteins and nuclein bases (enzyme inhibition or mutagenesis). Glutathione (GSH) is a peptide which is directly produced by the cells to counteract oxidative stress or harmful environmental influences such as, for example, increased mercury or lead exposure. The GSH content remaining after exposure to UVA radiation was determined by Hissin's method described in Anal. Biochem., 74, 214-226, 1976.

UVB rays initiate inflammation by activating an enzyme, namely phospholipase A2 or PLA2. This inflammation (erythema, edema) is induced by the removal of arachidonic acid from the phospholipids of the plasma membrane by the phospholipase. Arachidonic acid is the precursor of the prostaglandins which cause inflammation and cell membrane damage. The prostaglandins E2 (=PGE2) are formed by cyclooxygenase. The degree of release of the cytoplasm enzyme LDH (lactate dehydrogenase) in human keratinocytes serves as a marker for cell damage.

The extracts of the plant *Cassia alata* according to the invention reduce the effect of UVB radiation on the number of keratinocytes and on the content of released LDH. Accordingly, the extracts have the ability to reduce cell membrane damage caused by UVB radiation.

The present invention also relates to the use of extracts of the plant *Cassia alata* in cosmetic and/or dermatological anti-inflammatory care preparations.

In principle, the extracts according to the invention may be used as anti-inflammatory additives for any cosmetic and/or dermatological care preparations used against inflammation of the skin and hence in skin care. Anti-inflammatory care preparations in the context of the invention are understood to be the kind of care preparations which can heal or prevent inflammation of the skin. The inflammation may be caused by various factors.

In one particular embodiment of the invention, inflammation induced by UV radiation, skin contamination or bacterially or hormonally induced changes in the skin, for example acne, is treated.

The present invention also relates to the use of extracts of the plant *Cassia alata* as antioxidants or radical traps.

Antioxidants in the context of the invention are oxidation inhibitors which can be isolated from the plant *Cassia alata*. Antioxidants are capable of inhibiting or preventing changes caused by the effects of oxygen and other oxidative processes in the substances to be protected. The effect of antioxidants consists mainly in their acting as radical traps for the free radicals occurring during autoxidation.

Besides the use of extracts of the plant *Cassia alata* as antioxidants, other already known antioxidants may also be used. One possible use of the antioxidants, for example in cosmetic and/or dermatological preparations, is their use as secondary sun protection factors because antioxidants are capable of interrupting the photochemical reaction chain which is initiated when UV rays penetrate into the skin. Besides the plant extract according to the invention, other typical examples are amino acids (for example glycine, alanine, arginine, serine, threonine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene, lutein) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, boldin, boldo extract, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxy-butyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

The UV protection factors or antioxidants which may be used together with the extracts of *Cassia alata* may be added in quantities of 0.01 to 25, preferably 0.03 to 10 and more particularly 0.1 to 5% by weight, based on the total quantity in the preparations.

The present invention also relates to the use of extracts of *Cassia alata* in protective and restorative care preparations with skin revitalizing and reactivating activity. This way of using the care preparations has a positive effect, for example, on the adverse effects of environmental contamination of the skin by reactivating the natural functions of the skin hair and by making the skin hair more resistant. The revitalizing and reactivating activity of extracts of the plant *Cassia alata* counteracts apoptosis. In principle, the extracts according to the invention may be used as protective and restorative care preparations for any preparations which are used to prevent damage or to treat damage to the skin and hence in skin care. Another use in this field is application to sensitive skin damaged by allergies or other factors. The skin damage can have various causes.

The present invention also relates to the use of extracts of the plant *Cassia alata* in cosmetic and/or dermatological care preparations for stimulating the synthesis of dermal macromolecules selected from the group consisting of glycosaminoglycans, more particularly chondroitin sulfate, keratan sulfate, dermatan sulfate, hyaluronic acid and salts thereof, collagen, more particularly type III collagen, elastin, fibronectin, proteoglycans and salts thereof.

Dermal Macromolecules

Dermal macromolecules in the context of the invention are, in principle, any macromolecules which can be found as constituents of the skin either in the basal membrane between the dermis and the epidermis or directly in the dermis and epidermis. More particularly, the dermal macromolecules are in particular those selected from the group consisting of glycosaminoglycans, more particularly chondroitin sulfate, keratan sulfate, dermatan sulfate and hyaluronic acid and salts thereof, collagen, more particularly type III collagen, elastin, fibronectin, proteoglycans and salts thereof.

Glycosaminoglycans are also known as mucopolysaccharides and are negatively charged, long and unbranched polysaccharides (glycans) which consist of 1,4-linked units of disaccharides in which 1 mol of a uronic acid (D-glucuronic acid or, for example, L-iduronic acid) is glycosidically linked to the 3-position of an N-acetylated aminosugar (glycosamine). The glycosaminoglycans in the tissue are attached in several chains to a core protein and thus form proteoglycans. Chondroitin sulfate is a glycosaminoglycan. It occurs in the tissue as chondroitin-4-sulfate or as chondroitin-6-sulfate and consists inter alia of D-glucuronic acid and N-acetyl-D-galactosamine. It has a molecular weight of 5,000 to 50,000. The non-anticoagulating glycosaminoglycan dermatan sulfate, which is also known as beta-heparin, consists of L-iduronic acid or D-glucuronic acid, N-acetyl-D-galactosamine and sulfate groups. The molecular weight of dermatan sulfate is between 15,000 and 40,000. Hyaluronic acid is an acidic glycosaminoglycan. The basic unit of hyaluronic acid is an aminodisaccharide which is produced from D-glucuronic acid and N-acetyl-D-glucosamine in (beta 1-3) glycosidic linkage and which is attached to the next unit by a (beta 1-4) glycosidic bond. In contrast to many other glycosaminoglycans, hyaluronic acid does not carry any sulfate groups and is not protein-bound in the tissue.

Collagen consists of protein fibers and occurs in human skin in three different types (type 1, III and IV). In collagen, the individual polypeptide chains—which contain much of the amino acid proline and, as every third residue, glycine—are wound around one another to form a triple helix. The collagen fibers are synthesized as tropocollagen in the fibroblasts and are displaced into the extracellular matrix. The stimulation of the collagen synthesis in accordance with the invention leads to an increase in the production of collagen and hence to increased intermolecular stiffening of the dermis and thus to firmer looking skin. Elastin is also a fibrous protein. It consists of unstructured, covalently crosslinked polypeptide chains which form a rubber-like elastic material. After synthesis in the skin cells, the elastin is released into the extracellular matrix. The stimulation of the synthesis of the elastin polypeptide chains in accordance with the invention leads to an increase in the production of elastin and hence to an increase in the elasticity of the skin.

Fibronectin represents a group of high molecular weight glycoproteins (MW of the dimer ca. 440,000-550,000) which are found in the extracellular matrix and in extracellular fluids. By linear combination of three different, recurring domains, the fibronectin dimer (an elongate molecule measuring 600×25 Å) which is joined by two disulfide bridges binds inter alia collagens, glycosaminoglycans, proteoglycans, fibrin(ogen), deoxyribonucleic acids, immunoglobulins, plasminogen, plasminogen activator, thrombospondin, cells and microorganisms. These properties enable it, for example, to bind connective tissue cells to collagen fibrils or thrombocytes and fibroblasts to fibrin (contribution to wound healing).

Like the glycoproteins, the proteoglycans consist of carbohydrates and proteins. With the proteoglycans, however, the percentage content of polysaccharides is predominant. The proteoglycans of the skin contain dermatan sulfate. Around 140 such proteoglycans are non-covalently attached by small proteins (link proteins) to a hyaluronic acid chain to form molecular aggregates with an average molecular weight of ca. 2 million. The polyanionic aggregates, which are distinguished by their water binding capacity, are capable of forming solid gels which provide the supporting tissue (extracellular matrix) with elasticity and tensile strength. In mucosa, they protect the epithelia. The stimulation of the synthesis of proteoglycans and hyaluronic acid in accordance with the invention leads to a larger quantity of extracellular matrix and hence to greater elasticity and tensile strength.

The present invention also relates to the use of extracts of the plant *Cassia alata* in cosmetic and/or dermatological care preparations for reducing the proteolysis and glycation of dermal macromolecules, such as collagen, elastin, proteoglycans, in human skin by protease inhibition and, in particular, by inhibition of MMP, collagenase and/or elastase. Proteolysis is a process in which proteins are split by hydrolysis of the peptide bonds by acids or enzymes. Another name is proteinase digestion. The reduction in proteolysis in accordance with the invention leads to reduced cleavage of the dermal macromolecules with a protein structure and hence to prevention of any reduction in strengthening of the skin and to prevention of any decline in an increased elasticity. The *Cassia alata* extracts according to the invention act as protease inhibitors and more particularly as MMP and/or collagenase and/or elastase inhibitors. MMP are the initials for matrix metalloproteases. The matrix metalloproteases include collagenase and also a certain type of elastases. The activity of the enzymes is dependent on metal ions—in many cases $Zn^{2+}$ ions. The predominant elastase belongs to the group of serine proteases. Their catalytic reaction is based on another mechanism. These proteases (collagenase and the various elastases) catalyze the fragmentation and destruction of the dermal macromolecules, such as proteoglycan, collagen and elastin, and thus lead to ageing of the skin and to the effects of natural skin ageing after exposure to UV radiation.

Glycation is a non-enzymatic reaction of glucose or other sugars with proteins to form glycoproteins. This reaction results in unintended modifications to the collagen and elastin and hence in changes to the extracellular matrix. The function of the collagen and the extracellular matrix is disrupted. The prevention of glycation in accordance with the invention leads to a reduction in the non-enzymatic modification of collagen and elastin and hence to prevention of a reduced function of the extracellular matrix.

The preparations according to the invention may be used for the production of cosmetic and/or dermatological preparations such as, for example, foam baths, shower baths, creams, gels, lotions, alcohol and water/alcohol solutions, emulsions, wax/fat compounds, stick preparations, powders or ointments. These preparations may additionally contain mild surfactants, oil components, emulsifiers, pearlizing waxes, consistency factors, thickeners, superfatting agents, stabilizers, polymers, silicone compounds, fats, waxes, lecithins, phospholipids, biogenic agents, deodorants, antiperspirants, film formers, swelling agents, insect repellents, self-tanning agents, tyrosine inhibitors (depigmenting agents), hydrotropes, solubilizers, preservatives, perfume oils, dyes and the like as further auxiliaries and additives.

Surfactants

Suitable surfactants are anionic, nonionic, cationic and/or amphoteric or zwitterionic surfactants which may be present in the preparations in quantities of normally about 1 to 70% by weight, preferably 5 to 50% by weight and more preferably 10 to 30% by weight. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123-217. Typical examples of particularly suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, preferably based on wheat proteins.

Oil Components

Suitable oil components are, for example, Guerbet alcohols based on fatty alcohols containing 6 to 18 and preferably 8 to 10 carbon atoms, esters of linear $C_{6-22}$ fatty acids with linear or branched $C_{6-22}$ fatty alcohols, esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of $C_{18-38}$ alkylhydroxycarboxylic acids with linear or branched $C_{6-22}$ fatty alcohols (cf. DE 19756377 A1), more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates such as, for example, Dicaprylyl Carbonate (Cetiol® CC), Guerbet carbonates based on $C_{6-18}$ and preferably $C_{8-10}$ fatty alcohols, esters of benzoic acid with linear and/or branched $C_{6-22}$-alcohols (for example Finsolv® TN), linear or branched, symmetrical or nonsymmetrical dialkyl ethers containing 6 to 22 carbon atoms per alkyl group such as, for example, Dicaprylyl Ether (Cetiol® OE), ring opening products of epoxidized fatty acid esters with polyols, silicone oils (cyclomethicone, silicon methicone types, etc.) and/or aliphatic or naphthenic hydrocarbons, for example squalane, squalene or dialkyl cyclohexanes.

Emulsifiers

Suitable emulsifiers are, for example, nonionic surfactants from at least one of the following groups:

- products of the addition of 2 to 30 mol ethylene oxide and/or 0 to 5 mol propylene oxide onto linear $C_{8-22}$ fatty alcohols, onto $C_{12-22}$ fatty acids, onto alkyl phenols containing 8 to 15 carbon atoms in the alkyl group and alkylamines containing 8 to 22 carbon atoms in the alkyl group;
- alkyl and/or alkenyl oligoglycosides containing 8 to 22 carbon atoms in the alkyl group and ethoxylated analogs thereof;
- addition products of 1 to 15 mol ethylene oxide onto castor oil and/or hydrogenated castor oil;
- addition products of 15 to 60 mol ethylene oxide onto castor oil and/or hydrogenated castor oil;
- partial esters of glycerol and/or sorbitan with unsaturated, linear or saturated, branched fatty acids containing 12 to 22 carbon atoms and/or hydroxycarboxylic acids containing 3 to 18 carbon atoms and adducts thereof with 1 to 30 mol ethylene oxide;
- partial esters of polyglycerol (average degree of self-condensation 2 to 8), polyethylene glycol (molecular weight 400 to 5,000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and adducts thereof with 1 to 30 mol ethylene oxide;
- mixed esters of pentaerythritol, fatty acids, citric acid and fatty alcohol according to DE 1165574 PS and/or mixed esters of fatty acids containing 6 to 22 carbon atoms, methyl glucose and polyols, preferably glycerol or polyglycerol,
- mono-, di- and trialkyl phosphates and mono-, di- and/or tri-PEG-alkyl phosphates and salts thereof,
- wool wax alcohols,
- polysiloxane/polyalkyl/polyether copolymers and corresponding derivatives,
- block copolymers, for example Polyethyleneglycol-30 Dipolyhydroxystearate;
- polymer emulsifiers, for example Pemulen types (TR-1, TR-2) of Goodrich;
- polyalkylene glycols and
- glycerol carbonate.

The addition products of ethylene oxide and/or propylene oxide with fatty alcohols, fatty acids, alkylphenols or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE 2024051 PS.

Alkyl and/or alkenyl oligoglycosides, their production and their use are known from the prior art. They are produced in particular by reacting glucose or oligosaccharides with primary alcohols containing 8 to 18 carbon atoms. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide with the partial glycerides mentioned are also suitable.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide with the sorbitan esters mentioned are also suitable.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylolpropane or pentaerythritol with lauric acid, cocofatty acid, tallow fatty acid, palmitic acid, stearic acid, oleic acid, behenic acid and the like optionally reacted with 1 to 30 mol ethylene oxide.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethylimidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Finally, cationic surfactants are also suitable emulsifiers, those of the esterquat type, preferably methyl-quaternized difatty acid triethanolamine ester salts, being particularly preferred.

Fats and Waxes

Typical examples of fats are glycerides, i.e. solid or liquid, vegetable or animal products which consist essentially of mixed glycerol esters of higher fatty acids. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs). Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are normally classed as fats. Sphingosines and sphingolipids are also suitable.

Pearlizing Waxes

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Consistency Factors and Thickeners

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® and Pemulen types [Goodrich]; Synthalense [Sigma]; Keltrol types [Kelco]; Sepigel types [Seppic]; Salcare types [Allied Colloids]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Stabilizers

Metal salts of fatty acids such as, for example, magnesium, aluminium and/or zinc stearate or ricinoleate may be used as stabilizers.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinylimidazole polymers such as, for example, Luviquat® (BASF), condensation products of polyglycols and amines, quaternized collagen polypeptides such as, for example, Lauryidimonium Hydroxypropyl Hydrolyzed Collagen (Lamequat® L, Grunau), quaternized wheat polypeptides, polyethyleneimine, cationic silicone polymers such as, for example, Amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2252840 A and crosslinked water-soluble polymers thereof, cationic chitin derivatives such as, for example, quaternized chitosan, optionally in micro-crystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacryl-amide/methyl methacrylate/tert.- butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones. Other suitable polymers and thickeners can be found in Cosm. Toil. 108, 95 (1993).

Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Biogenic Agents

Biogenic agents in the context of the invention are, for example, tocopherol, tocopherol acetate, tocopherol palmitate, ascorbic acid, deoxyribonucleic acid and fragmentation products thereof, retinol, bisabolol, allantoin, phytantriol, panthenol, AHA acids, amino acids, ceramides, pseudoceramides, essential oils, plant extracts and additional vitamin complexes.

Deodorants and Germ Inhibitors

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers. Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of labdanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic fragrances. Natural fragrances include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxy-citronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyric, citronellol, phenylethyl alcohol, α-hexyl-cinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Antiperspirants reduce perspiration and thus counteract underarm wetness and body odor by influencing the activity of the eccrine sweat glands. Aqueous or water-free antiperspirant formulations typically contain the following ingredients:

astringent active principles,
oil components,
nonionic emulsifiers,
co-emulsifiers,
consistency factors,
auxiliaries in the form of, for example, thickeners or complexing agents and/or
non-aqueous solvents such as, for example, ethanol, propylene glycol and/or glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example,

- inflammation-inhibiting, skin-protecting or pleasant-smelling essential oils,
- synthetic skin-protecting agents and/or
- oil-soluble perfume oils.

Typical water-soluble additives are, for example, preservatives, water-soluble perfumes, pH regulators, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Swelling Agents

Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

Insect Repellents

Suitable insect repellents are N,N-diethyl-m-toluamide, pentane-1,2-diol or Ethyl Butylacetylaminopropionate.

Self-Tanning Agents and Depigmenting Agents

A suitable self-tanning agent is dihydroxyacetone. Suitable tyrosine inhibitors which prevent the formation of melanin and are used in depigmenting agents are, for example, arbutin, ferulic acid, koji acid, coumaric acid and ascorbic acid (vitamin C).

Hydrotropes

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are

- glycerol;
- alkylene glycols such as, for example, ethylene glycol, diethylene glycol, propylene glycol, butylene glycol, hexylene glycol and polyethylene glycols with an average molecular weight of 100 to 1000 dalton;
- technical oligoglycerol mixtures with a degree of self-condensation of 1.5 to 10 such as, for example, technical diglycerol mixtures with a diglycerol content of 40 to 50% by weight;
- methylol compounds such as, in particular, trimethylol ethane, trimethylol propane, trimethylol butane, pentaerythritol and dipentaerythritol;
- lower alkyl glucosides, particularly those containing 1 to 8 carbon atoms in the alkyl group, for example methyl and butyl glucoside;
- sugar alcohols containing 5 to 12 carbon atoms, for example sorbitol or mannitol,
- sugars containing 5 to 12 carbon atoms, for example glucose or sucrose;
- amino sugars, for example glucamine;
- dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils

Suitable perfume oils are mixtures of natural and synthetic fragrances. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxy-citronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106. These dyes are normally used in concentrations of 0.001 to 0.1% by weight, based on the mixture as a whole.

EXAMPLES

Example 1

Extraction of the Plants with Distilled Water 300 g dried *Cassia alata* leaves were coarsely size-reduced in a blade-equipped size-reducing machine and then transferred to a glass reactor containing 1 liter distilled water. The infusion was heated to between 85 and 90° C. and extracted at that temperature with stirring for 1 hour. The mixture was then cooled to 20° C. and centrifuged for 20 mins. at a speed of 5000 G. The supernatant liquid was separated from the insoluble residue by filtration through depth filters with a mean porosity of 450 nm (from Seitz of Bordeaux, France). The extract was brown in color. It was spray-dried at a starting temperature of 185° C. and an end temperature of 80° C. Another way of drying the extract is freeze-drying. Plants from three different countries (Ghana, India and Benin) were extracted. The yield of dry product was 12.4 to 18.7% by weight, based on the dry weight of plants used.

TABLE 1

Yields of dry product of the extracted plant after extraction with distilled water

| Country of origin | Batch | Yield (% by weight) | Drying method |
|---|---|---|---|
| Ghana | A | 13.5 | Freeze-drying |
| India | B | 18.7 | Spray drying |
| Benin | C | 12.4 | Spray drying |

Example 2

Extraction of the Plants with Aqueous Methanol

Example 1 was repeated except that extraction was carried out with 1 liter 50% by weight aqueous methanol. Extraction was carried out with stirring for 1 hour at a temperature of 80 to 85° C. and the extract was further processed as described above. Filtration was carried out as described in Example 1. Thereafter the alcohol was removed under reduced pressure at 35° C. and the brown residue was then spray-dried or freeze-dried as described. The yield of dry product was 15.1 to 18.4%, based on the dry weight of plants used.

TABLE 2

Yields of dry product of the extracted plant after extraction with 50% aqueous methanol

| Country of origin | Batch | Yield (% by weight) | Drying method |
|---|---|---|---|
| Ghana | A | 18.4 | Freeze-drying |
| India | B | 15.1 | Spray drying |
| Benin | C | 15.2 | Spray drying |

Example 3

Anti-Oxidative and Radical-Trapping Properties

In a first series of tests, the extracts were investigated for their performance against oxidative stress. The extracts of Examples 1 and 2 were used in various concentrations. In a first test, the hydroxylation of salicylic acid by hydroxyl radicals (from the reaction of hydrogen peroxide with iron (III) ions and EDTA) was investigated as a reference system. This reaction can be photometrically investigated because the hydroxylation product of salicylic acid is reddish in color. The influence of the extracts on the formation of hydroxysalicylic acid was measured at an optical density of 490 nm. The results are set out in Table 1 as the concentration in w/v (weight per volume) of Cassia alata extract required for 50% inhibition ($IC_{50}$% w/v) of hydroxylation.

TABLE 3

Concentration of extract for 50% inhibition of hydroxylation

| | Extract of Example 1 | | | Extract of Example 2 | | |
|---|---|---|---|---|---|---|
| Batch | A | B | C | A | B | C |
| $IC_{50}$ % w/v | 0.18 | 0.06 | 0.07 | 0.33 | 0.10 | 0.12 |

The results set out in Table 3 show that the extracts of the plant Cassia alata used are active against radicals. Extracts differing in their activity according to the extraction process used are obtained. Using the extraction process described in Example 1 for example, a concentration of 0.06% w/v is sufficient to obtain a 50% inhibition of the radical reaction. In this case, the formation of hydroxysalicylic acid by hydroxy radicals is reduced by 50% at that concentration.

In a third test, xanthine oxidase was selected as the test system. Under oxidative stress, the enzyme converts purine bases, such as adenine or guanine for example, into uric acid. The oxygen radicals formed as intermediates can be detected and quantitatively determined by reaction with luminol (through the luminescence). The luminescence yield decreases in the presence of substances with radical-trapping properties.

TABLE 4

Degree of luminescence

| | Extract of Example 1 | | | Extract of Example 2 | | |
|---|---|---|---|---|---|---|
| Batch | A | B | C | A | B | C |
| $IC_{50}$ % w/v | 0.015 | 0.007 | 0.007 | 0.009 | 0.006 | 0.005 |

It can be seen from Table 4 that the extracts of the plant Cassia alata inhibit the radical-induced formation of luminescence. A concentration of only 0.005% w/v of the extract of Example 2 provides 50% inhibition of luminescence and accordingly shows distinct radical-trapping properties.

Example 4

Inhibition of Aptosis Induction

Background:

In contrast to necrosis, apoptosis is understood to be the natural, controlled cell death of certain unwanted or damaged cells. It is an active cell process (suicide on command). Apoptosis is initiated by oxidative stress (UV radiation, inflammation), by a deficiency of growth factors or by toxins (pollutants, genotoxins, etc.). In the skin ageing process, for example, apoptosis of the skin cells can be induced by a deficiency of growth factors in the skin. In the apoptosis-affected cells, the nuclear DNA is degraded by the specific enzyme endonuclease and the DNA fragments are released into the cytoplasm.

Method:

The ability of the plant extracts of Cassia alata to prevent apoptosis induced by a deficiency of growth factors in human skin cells was investigated. The test was conducted in vitro on human fibroblasts and human keratinocytes. The human cells were cultivated in a nutrient medium (DMEM=Dulbecco Minimum Essential Medium from Life Technologie S.a.r.l.) containing 10% of foetal calf serum (from Dutcher). Bromodeoxyuridine (BrdU) was added to this nutrient medium. It was incorporated in the DNA and was subsequently used to detect the DNA fragments in the cytoplasm. After two days' incubation, the nutrient medium was replaced by nutrient medium (DMEM) with no foetal calf serum. The active substance to be tested was added. For the plant extract, three different batches, i.e. two different extracts (batches A, B and C) obtained by the same extraction method, were tested. For comparison, a cell sample was incubated without any active substance to be tested (quantities and concentrations shown in Tables 5 and 6).

After incubation for one or two days at 37° C., the cells were recovered by trypsination using the Dunnebacke and Zitcer method described in Cell and Tissue Culture, Ed.: J. Paul, Churchill Livingstone, 1975, p. 226. After the trypsin treatment, the cells were centrifuged and counted. The BrdU content in DNA fragments from the cytoplasm was then determined by the ELISA Test (ELISA Kit from Roche). The BrdU content is a measure of the DNA fragments released into the cytoplasm from the nucleus, the cell core. The results were based on one million cells and were expressed in percent by comparison with the control. The results are set out in the following Tables lead to cell death. The number of intact cells present has hardly changed whereas the content of DNA fragments in the cytoplasm is reduced by comparison with the control under the influence of the plant extract. Selective cell death is suppressed by these plant extracts. The plant extracts have an effect similar to the growth factor and hence an anti-ageing effect on human skin cells.

Example 5

Anti-Inflammatory Properties In Vitro—UVB Protection

Background:

UVB rays cause inflammation (erythema, edema) by activating an enzyme, namely phospholipase A2 or PLA2, which removes arachidonic acid from the phospholipids of the cell membrane. Arachidonic acid is the precursor of the prostaglandins which cause inflammation and cell membrane damage; the prostaglandins E2 (=PGE2) are formed by cyclooxygenase.

TABLE 5

Number of cells and content of DNA fragments in the cytoplasm after treatment of human fibroblasts with Cassia alata extracts

| Cell counting | Batch | | | Content of DNA fragments | Batch | | |
|---|---|---|---|---|---|---|---|
| | A | B | C | | A | B | C |
| Control | 100 | 100 | 100 | Control | 100 | 100 | 100 |
| Extract of Example 2; 0.01% by weight | 104 | 106 | 149 | Extract of Example 2; 0.01% by weight | 23 | 85 | 94 |
| Extract of Example 2; 0.02% by weight | 122 | 112 | 146 | Extract of Example 2; 0.02% by weight | 11 | 76 | 59 |

TABLE 6

Number of cells and content of DNA fragments in the cytoplasm after treatment of human keratinocytes with Cassia alata extracts

| Cell counting | Batch | | | Content of DNA fragments | Batch | | |
|---|---|---|---|---|---|---|---|
| | A | B | C | | A | B | C |
| Control | 100 | 100 | 100 | Control | 100 | 100 | 100 |
| EGF 30 ng/ml | 121 | | | EGF 30 ng/ml | 32 | | |
| Extract of Example 1; 0.01% by weight | | 105 | | Extract of Example 1; 0.01% by weight | | 63 | |
| Extract of Example 1; 0.02% by weight | 105 | | 101 | Extract of Example 1; 0.02% by weight | 39 | | 63 |
| Extract of Example 1; 0.05% by weight | 108 | 105 | 103 | Extract of Example 1; 0.05% by weight | 25 | 47 | 48 |
| Control | 100 | 100 | 100 | Control | 100 | 100 | 100 |
| Extract of Example 2; 0.01% by weight | 104 | 106 | 149 | Extract of Example 2; 0.01% by weight | 23 | 85 | 94 |
| Extract of Example 2; 0.02% by weight | 122 | 112 | 146 | Extract of Example 2; 0.02% by weight | 11 | 76 | 59 |

It can be seen from the results set out in Tables 5 and 6 that the use of Cassia alata extracts reduces apoptosis in human cell cultures in vitro. The content of free DNA fragments in the cytoplasm and hence the degree of destroyed DNA in the cell core and the degree of apoptosis decrease with increasing concentration of Cassia alata extract. By comparison with the known growth factor Epidermal Growth Factor (EGF) which was added in a concentration of 30 ng/ml instead of the plant extract, the plant extract is just as effective in reducing apoptosis The cell counts document the fact that the plant extracts according to the invention are non-toxic and do not Method:

The effect of UVB radiation was investigated in vitro in keratinocytes by determining the release of the cytoplasm enzyme LDH (lactate dehydrogenase). This enzymes serves as a marker for cell damage.

To carry out the tests, a defined medium containing foetal calf serum was inoculated with the keratinocytes and the plant extract (diluted with saline solution) was added 72 hours after the inoculation.

The keratinocytes were then exposed to a dose of UVB (30 mJ/cm$^2$-tubes: DUKE GL40E).

After incubation for another day at 37° C./5% $CO_2$, the LDH and PGE2 content in the supernatant was determined. The LDH (lactate dehydrogenase) content was determined by an enzyme reaction (kit used to determine LDH levels from Roche). The PGE2 content was determined by an ELISA test (ELISA kit from Roche). To determine the DNA in the cytoplasm of the keratinocytes, bromodeoxyuridine (BrDU) was added to the growth medium as described in the previous Example. After the trypsin treatment, the cells were centrifuged and counted. The BrDU content in DNA fragments from the cytoplasm was then determined by the ELISA test. The number of adhering keratinocytes was determined (after trypsin treatment) with a particle counter.

TABLE 7

Cell protecting effect of an extract of Cassia alata against UVB rays; results in % based on the control, average value of 2 tests each repeated twice.

| Extract of Example 1 | Number of keratinocytes | | | Content of LDH released | | |
|---|---|---|---|---|---|---|
| | A | B | C | A | B | C |
| Control without UV | 331 | 195 | 200 | 0 | 0 | 0 |
| Control with UVB (315 nm) | 100 | 100 | 100 | 100 | 100 | 100 |
| UVB + extract 0.01% | 109 | 114 | 282 | 87 | 131 | 0 |
| UVA + extract 0.05% | 189 | 118 | 295 | 24 | 82 | 0 |

| Extract of Example 1 | Content of PGE2 released | | | Content of DNA fragments | |
|---|---|---|---|---|---|
| | A | B | C | B | C |
| Control without UV | 0 | 0 | 0 | 0 | 0 |
| Control with UVB (315 nm) | 100 | 100 | 100 | 100 | 100 |
| UVB + extract 0.01% | 112 | 75 | 0 | — | 57 |
| UVA + extract 0.05% | 40 | 91 | 0 | 27 | 9 |

| Extract of Example 2 | Number of keratinocytes | | | Content of LDH released | | |
|---|---|---|---|---|---|---|
| | A | B | C | A | B | C |
| Control without UV | 331 | 173 | 188 | 0 | 0 | 0 |
| Control with UVB (315 nm) | 100 | 100 | 100 | 100 | 100 | 100 |
| UVB + extract 0.01% | 258 | 178 | — | 14 | 25 | — |
| UVB + extract 0.02% | 369 | 220 | 337 | 19 | 10 | 2 |
| UVA + extract 0.05% | — | 226 | 354 | — | 18 | 7 |

| Extract of Example 2 | Content of PGE2 released | | | Content of DNA fragments | |
|---|---|---|---|---|---|
| | A | B | C | B | C |
| Control without UV | 0 | 0 | 0 | 0 | 0 |
| Control with UVB (315 nm) | 100 | 100 | 100 | 100 | 100 |
| UVB + extract 0.01% | 35 | 208 | — | — | 63 |
| UVB + extract 0.02% | 19 | 78 | 12 | 55 | 62 |
| UVA + extract 0.05% | — | — | 14 | 44 | 90 |

The results of these tests show that an extract of the plant Cassia alata according to the invention reduces the effect of UVB radiation on the number of keratinocytes and on the content of LDH released. There is a reduction in the PGE2 content induced by UVB in human keratinocytes, a reduction in the content of LDH released and a reduction in DNA fragments in the cytoplasm. Accordingly, the described extracts have the ability to reduce cell membrane damage caused by UVB radiation and inhibit UVB-induced inflammation.

Example 6

Demonstration of the Stimulation of Dermal Macromolecules (GAGs)

Background:

The object of these tests is to demonstrate the stimulating activity of *Cassia alata* extracts on the synthesis of dermal macromolecules on human fibroblast cultures in vitro.

The dermis is made up of cells (fibroblasts and mast cells), tissue constituents (collagen and elastin) and so-called basic substances. These basic substances include macromolecules such as, for example, glycosaminoglycans (GAGs), hyaluronic acid, chondroitin sulfate, dermatan sulfate and glycoproteins. Ageing of the skin results in a reduction in the intermolecular strength and elasticity of the dermis and hence in the firmness of the skin. The number of skin cells present, especially the fibroblasts, is also reduced by ageing. The collagen fibers gradually become fragmented and the ratio of insoluble to soluble collagen increases. The fine dermal elastic fibers become coarse and are destroyed. The synthesis of GAG (glycosaminoglycan) is reduced. All these processes contribute towards ageing of the skin and its manifestations, such as wrinkles and lack of firmness of the skin.

Using the following model, the stimulation of the synthesis of the dermal macromolecules can be demonstrated and an active substance capable of acting against ageing of the skin, i.e. as an anti-ageing agent, thus identified.

Method:

The measuring technique is based on the coloring of macromolecules in a culture of human fibroblasts which, with type I collagen, forms a collagen gel or collagen lattice fibers. Using coloring reagents, certain regions of these fibers were quantified for the percentage content of the macromolecules mentioned.

To this end, a suspension of human fibroblasts was mixed with a solution of type I collagen (1-2 mg/ml). The resulting mixture was incubated in a defined nutrient medium (DMEM=Dulbecco Minimum Essential Medium, a product of Life Technologie S.a.r.l.) containing 0.5 or 2% by weight fetal calf serum (FCS) for 14 days at 37° C. in a 5% $CO_2$ atmosphere in Petri dishes (5 ml per dish), the plant extracts to be tested being added in various concentrations.

The kinetics of the collagen gel concentration were determined 2-3 times per week by measuring two perpendicular diameters on each collagen gel using a microscope with an image analyzing system. The size of the area is shown in $cm^2$ in Table 8. After 14 days' incubation, the density of the collagen gel was determined by image analysis using a light source of visible light by comparatively analyzing various gray stages, i.e. by relative determination of the density (0=clear or white and 1=black) which cannot be provided with a unit.

After seven and after 14 days' incubation, biopsies (tissue samples) were taken and histological sections of the collagen gel containing human fibroblasts were obtained. The synthesis of macromolecules was quantified by the coloring of glycosaminoglycan with PAS Alcian blau, for example from SIGMA, by the Periodic Acid Schiff (PAS) method described in Mowry R. W., Anal. NY Acad. Sci. 106, Art. 2, 402, 1963. The stimulation of the synthesis of macromolecules was directly evaluated in the vicinity of fibroblasts. This zone is also known as the "perifibroblast area".

The "perifibroblast" secretion or the secretion of fibroblasts into the periphery was quantified with an image analyzer and microscope. Reactive structures in the "perifibroblast area" were detected and the various gray stages were comparatively determined. The values of the grey stages were subdivided from 0=white to 255=black. These parameters are directly proportional to the intensity of the synthesis of macromolecules and hence to the percentage content of GAGs in the fibroblasts. The results of the values of these parameters are shown in the following Table and may be directly regarded as representative values for the synthesis activity of the fibroblasts. The percentage GAG content is described as a relative value of the grey stage.

TABLE 8

Content of GAGs in tisue samples of human fibroblasts containing collagen after treatment with Cassia alata extract

|  | Area [cm$^2$] | | Density | GAGs content | |
|---|---|---|---|---|---|
|  | 7 days | 14 days | 14 days | 7 days | 14 days |
| Extract of Example 1 | | | | | |
| FCS 0.5% by weight | 7.6 | 4.4 | 0.36 | 12.25 | 10.76 |
| FCS 0.5 + Cassia alata 0.003% by weight | 7.3 | 4.2 | 0.33 | 11.21 | 12.54 |
| FCS 0.5 + Cassia alata 0.01% by weight | 10.3 | 5.9 | 0.27 | 11.09 | 15.36 |
| (FCS 2% by weight) | 4.3 | 3.2 | 0.38 | 11.27 | 15.14 |
| Extract of Example 2 | | | | | |
| FCS 0.5% by weight | 6.1 | 5.1 | — | 13.6 | — |
| FCS 0.5 + Cassia alata 0.003% by weight | 11.5 | 5.3 | 0.28 | 17.1 | 19.5 |
| FCS 0.5 + Cassia alata 0.01% by weight | 19.6 | 19.6 | 0.08 | — | — |
| (FCS 2% by weight) | 3.0 | 2.5 | 0.45 | 14.9 | 15.0 |

The results of the determination of the percentage glycosaminoglycan content in tissue samples of collagen gel containing fibroblasts, especially in the "perifibroblast area", show a significant increase in the percentage of macromolecules after 14 days' incubation with various concentrations of *Cassia alata* extract of Example 1 by comparison with incubation with pure fetal calf serum (FCS) in a concentration of 0.5% by weight. The extract of Example 2 also leads to a marked increase in the GAG content in a concentration of only 0.003% by weight. These values prove that an extract of the plant *Cassia alata* stimulates the synthesis of glycosaminoglycan (GAG) in fibroblasts.

The results also prove that the extracts of *Cassia alata* have a high capacity for stimulating the metabolism of fibroblasts. The extracts show regenerating and revitalizing activity on human fibroblasts and may therefore be used as energy sources and as anti-ageing ingredients in cosmetic and dermatological preparations.

Example 7

Cell Protecting Effect Against UVA on Human Fibroblasts Cultivated In Vitro

Background:

UVA rays penetrate into the dermis where they lead to oxidative stress which is demonstrated by lipoperoxidation of the cytoplasm membranes.

The lipoperoxides are degraded to malonaldialdehyde which will crosslink many biological molecules, such as proteins and nuclein bases (enzyme inhibition or mutagenesis).

Glutathione (GSH) is a peptide which is directly produced by the cells to counteract oxidative stress or harmful environmental influences such as, for example, increased mercury or lead exposure. The GSH content remaining after exposure to UVA radiation was determined by Hissin's method described in Anal. Biochem., 74, 214-226, 1976.

Method:

To carry out these tests, a defined culture medium (DMEM) containing 10% fetal calf serum was inoculated with the fibroblasts and added to the plant extract (in the defined medium containing 2% serum) 72 hours after inoculation.

After incubation for 48 hours at 37° C./5% $CO_2$, the culture medium was replaced by a saline solution and the fibroblasts were exposed to a dose of UVA (3 to 15 J/cm$^2$; tubes: MAZDA FLUOR TFWN40).

After the exposure to UVA, the cell protein content, the GSH content and the MDA level (malonaldialdehyde level) in the supernatant saline solution were quantitatively determined by reaction with thiobarbituric acid. The results are shown in percent by comparison with the control with no exposure.

TABLE 9

Quantification of malonaldialdehyde in fibroblasts (results in %, based on the control, average value of 2 tests each repeated three times)

| Concentration (% by weight) | MDA level | | Cell protein content | | GSH content | |
|---|---|---|---|---|---|---|
| Extracts of Ex. 2 - Batch No. | C | B | C | B | C | B |
| Control without UV | 0 | 0 | 100 | 100 | 100 | 100 |
| UVA (3 to 15 J/cm$^2$) | 100 | 100 | 93 | 81 | 78 | 94 |
| UVA + extract 0.01% | 42 | 81 | 100 | 121 | 114 | 88 |
| UVA + extract 0.02% | 35 | 63 | 98 | 120 | 137 | 87 |

The results set out in Table 9 show that the extracts according to the invention of *Cassia alata* leaves significantly reduce the level of MDA in human fibroblasts which is induced by UVA radiation. The results reflect a high capacity on the part of batch C to keep the GSH content in human fibroblasts relatively constant after exposure to UVA radiation. The results reflect also a high capacity on the part of extracts of the leaves of *Argania spinosa* to reduce the harmful effects of oxidative stress on the skin.

Example 8

Inhibition of Elastase Activity

Elastase is a protease which is secreted by the fibroblasts either during inflammation by the leucocytes or as a result of UVA damage and which is jointly responsible for the degradation of dermal macromolecules, for example collagen and elastin, and hence for ageing of the skin. In order to determine the effectiveness of the plant extract in inhibiting the release of elastase, pancreas elastase (a serine protease) was investigated and elastin was marked with a chromogenic synthetic substrate as substrate. The system was incubated with the active ingredients for 30 mins. at room temperature and, after centrifuging, the optical density of the dye at 520 nm was determined. The extracts were used in a quantity of 0.3% by weight. The results are set out in Table 10, again relative to a control (α1-antitrypsin) as standard (=0%).

TABLE 10

| Elastase inhibition | |
| --- | --- |
| Extract of Example 2 | Inhibition [%] |
| Batch B | 34 |
| Batch C | 54 |

The results show that *Cassia alata* extracts are capable of inhibiting elastase and especially pancreas elastase. This can be attributed inter alia to inhibition of the release of elastase.

Example 9

Inhibition of the Glycation of Collagen

To show that the *Cassia alata* extracts inhibit the non-enzymatic glycation of macromolecules, type I collagen was treated with glucose and the extracts for 21 d at 45° C. The suspensions were then centrifuged and the content of Schiff's bases in the supernatant liquid was determined by fluorescence measurement at 430 nm. The results are set out in Table 11, again based on the control as standard (without extract and without glucose).

TABLE 11

Inhibition of glycation of collagen (B1 and B2 are extracts of raw material from India)

| | Extract of Example 1 | | Extract of Example 2 | |
| --- | --- | --- | --- | --- |
| | Batch A | Batch C | Batch B1 | Batch B2 |
| Control without glucose | 46 | 54 | 54 | 54 |
| Control with glucose | 100 | 100 | 100 | 100 |
| Glucose + extract 0.1% | 73 | 73 | 66 | 51 |

The results show that *Cassia alata* extracts are capable of inhibiting the glycation of collagen and hence of inhibiting the ageing process of the dermis by glycation of collagen fibers.

Accordingly, the effects and positive activities of the *Cassia alata* extracts contain a very marked

- stimulating, revitalizing and regenerating activity on the metabolism and hence anti-ageing activity
- apoptosis-inhibiting activity and hence anti-ageing activity and
- cell protecting effect against inflammation, particularly UVB-induced inflammation
- radical-trapping properties
- cell protecting effect against oxidative stress, particularly UVA-initiated stress
- proteolysis- and glycation-inhibiting activity.

Example 10

Exemplary Formulations of Cosmetic Products Containing *Cassia alata* Extracts The *Cassia alata* extracts obtained in accordance with Examples 1 and 2 were used in the following formulations according to the invention K1 to K21 and 1 to 23. The cosmetic preparations thus produced showed very good skincare properties coupled with high dermatological compatibility in relation to the comparison formulations C1, C2 and C3. In addition, the preparations according to the invention proved to be stable to oxidative decomposition.

TABLE 12

Soft cream formulations K1 to K7
(All quantities in % by weight, based on the cosmetic preparation)

| INCI name | K1 | K2 | K3 | K4 | K5 | K6 | K7 | C1 |
| --- | --- | --- | --- | --- | --- | --- | --- | --- |
| Glyceryl Stearate (and) Ceteareth-12/20 (and) Cetearyl Alcohol (and) Cetyl Palmitate | 8.0 | 8.0 | 8.0 | 8.0 | 8.0 | 8.0 | 8.0 | 8.0 |
| Cetearyl Alcohol | 2.0 | 2.0 | 2.0 | 2.0 | 2.0 | 2.0 | 2.0 | 2.0 |
| Dicaprylyl Ether | 2.0 | 2.0 | 2.0 | 2.0 | 2.0 | 2.0 | 2.0 | 2.0 |
| Cocoglycerides | 3.0 | 3.0 | 3.0 | 3.0 | 3.0 | 3.0 | 3.0 | 3.0 |
| Cetearyl Isononanoate | 3.0 | 3.0 | 3.0 | 3.0 | 3.0 | 3.0 | 3.0 | 3.0 |
| Glycerin (86% by weight) | 3.0 | 3.0 | 3.0 | 3.0 | 3.0 | 3.0 | 3.0 | 3.0 |
| Extract of Example 1 or 2 | 0.5 | 0.5 | 0.5 | 0.5 | 0.5 | 0.5 | 0.5 | — |
| Tocopherol | | 0.5 | | | | | | |
| Allantoin | | | 0.2 | | | | | |
| Bisabolol | | | | 0.5 | | | | |
| Chitosan (Hydagen CMF) | | | | | 10.0 | | | |
| Deoxyribonucleic acid[1)] | | | | | | 0.5 | | |
| Panthenol | | | | | | | 0.5 | |
| Water | | | | to 100 | | | | |

TABLE 13

Night cream formulations K8 to K14
(All quantities in % by weight, based on the cosmetic preparation)

| INCI name | K8 | K9 | K10 | K11 | K12 | K13 | K14 | C2 |
| --- | --- | --- | --- | --- | --- | --- | --- | --- |
| Polyglyceryl-2 Dipolyhydroxystearate | 4.0 | 4.0 | 4.0 | 4.0 | 4.0 | 4.0 | 4.0 | 5.0 |
| Polyglyceryl-3 Diisostearate | 2.0 | 2.0 | 2.0 | 2.0 | 2.0 | 2.0 | 2.0 | 2.0 |
| Cera Alba | 2.0 | 2.0 | 2.0 | 2.0 | 2.0 | 2.0 | 2.0 | 2.0 |
| Zinc Stearate | 2.0 | 2.0 | 2.0 | 2.0 | 2.0 | 2.0 | 2.0 | 2.0 |

TABLE 13-continued

Night cream formulations K8 to K14
(All quantities in % by weight, based on the cosmetic preparation)

| INCI name | K8 | K9 | K10 | K11 | K12 | K13 | K14 | C2 |
|---|---|---|---|---|---|---|---|---|
| Cocoglycerides | 3.0 | 3.0 | 3.0 | 3.0 | 3.0 | 3.0 | 3.0 | 3.0 |
| Cetearyl Isononanoate | 8.0 | 8.0 | 8.0 | 8.0 | 8.0 | 8.0 | 8.0 | 8.0 |
| Dicaprylyl Ether | 5.0 | 5.0 | 5.0 | 5.0 | 5.0 | 5.0 | 5.0 | 5.0 |
| Magnesium sulfate | 1.0 | 1.0 | 1.0 | 1.0 | 1.0 | 1.0 | 1.0 | 1.0 |
| Glycerin (86% by weight) | 5.0 | 5.0 | 5.0 | 5.0 | 5.0 | 5.0 | 5.0 | 5.0 |
| Extract of Example 1 or 2 | 0.5 | 0.5 | 0.5 | 0.5 | 0.5 | 0.5 | 0.5 | — |
| Tocopherol | | 0.5 | | | | | | |
| Allantoin | | | 0.2 | | | | | |
| Bisabolol | | | | 0.5 | | | | |
| Chitosan (Hydagen CMF) | | | | | 10.0 | | | |
| Deoxyribonucleic acid[1] | | | | | | 0.5 | | |
| Panthenol | | | | | | | 0.5 | |
| Water | | | | to 100 | | | | |

TABLE 14

W/O body lotion formulations K15 to K21.
(All quantities in % by weight, based on the cosmetic preparation)

| INCI name | K15 | K16 | K17 | K18 | K19 | K20 | K21 | C3 |
|---|---|---|---|---|---|---|---|---|
| PEG-7 Hydrogenated Castor Oil | 7.0 | 7.0 | 7.0 | 7.0 | 7.0 | 7.0 | 7.0 | 7.0 |
| Decyl Oleate | 7.0 | 7.0 | 7.0 | 7.0 | 7.0 | 7.0 | 7.0 | 7.0 |
| Cetearyl Isononanoate | 7.0 | 7.0 | 7.0 | 7.0 | 7.0 | 7.0 | 7.0 | 7.0 |
| Glycerin (86% by weight) | 5.0 | 5.0 | 5.0 | 5.0 | 5.0 | 5.0 | 5.0 | 5.0 |
| $MgSO_4.7H_2O$ | 1.0 | 1.0 | 1.0 | 1.0 | 1.0 | 1.0 | 1.0 | 1.0 |
| Extract of Example 1 or 2 | 1.5 | 1.5 | 1.5 | 1.5 | 1.5 | 1.5 | 1.5 | — |
| Tocopherol | | 0.5 | | | | | | |
| Allantoin | | | 0.2 | | | | | |
| Bisabolol | | | | 0.5 | | | | |
| Chitosan (Hydagen CMF) | | | | | 10.0 | | | |
| Deoxyribonucleic acid[1] | | | | | | 0.5 | | |
| Panthenol | | | | | | | 0.5 | |
| Water | | | | to 100 | | | | |

[1] Deoxyribonucleic acid: molecular weight ca. 70,000, purity (determined by spectrophotometric measurement of absorption at 260 nm and 280 nm): at least 1.7

TABLE 15

Cosmetic preparations (all quantities in % by weight, based on the cosmetic preparation, water, preservative add up to 100% by weight)

| Composition (INCI) | 1 | 2 | 3 | 4 |
|---|---|---|---|---|
| Texapon ® NSO<br>Sodium Laureth Sulfate | 38.0 | 38.0 | 25.0 | — |
| Texapon ® SB 3<br>Disodium Laureth Sulfosuccinate | — | — | 10.0 | — |
| Plantacare ® 818<br>Coco Glucosides | 7.0 | 7.0 | 6.0 | — |
| Plantacare ® PS 10<br>Sodium Laureth Sulfate (and) Coco Glucosides | — | — | — | 20.0 |
| Dehyton ® PK 45<br>Cocamidopropyl Betaine | — | — | 10.0 | — |
| Lamesoft ® PO 65<br>Coco-Glucoside (and) Glyceryl Oleate | 3.0 | | | 4.0 |
| Lamesoft ® LMG<br>Glyceryl Laurate (and) Potassium Cocoyl Hydrolyzed Collagen | — | 5.0 | — | — |
| Euperlan ® PK 3000 AM<br>Glycol Distearate (and) Laureth-4 (and) Cocamidopropyl Betaine | — | 3.0 | 5.0 | 5.0 |
| Cassia alata extract of Example 1 or 2 | 1.0 | 1.0 | 1.0 | 1.0 |
| Arlypon ® F<br>Laureth-2 | 3.0 | 3.0 | 1.0 | — |
| Sodium Chloride | — | 1.5 | — | 1.5 |

(1-2) shower bath, (3) shower gel, (4) wash lotion

TABLE 15

Cosmetic preparations "2-in-1" shower bath (water, preservative to 100% by weight)

| Composition (INCI) | 5 | 6 | 7 | 8 |
|---|---|---|---|---|
| Texapon ® NSO<br>Sodium Laureth Sulfate | 30.0 | 25.0 | — | 25.0 |
| Plantacare ® 818<br>Coco Glucosides | — | — | — | 8.0 |
| Plantacare ® 2000<br>Decyl Glucoside | — | 8.0 | — | — |
| Plantacare ® PS 10<br>Sodium Laureth Sulfate (and) Coco Glucosides | — | — | 20.0 | — |
| Dehyton ® PK 45<br>Cocamidopropyl Betaine | — | 10.0 | 10.0 | — |
| Lamesoft ® PO 65<br>Coco-Glucoside (and) Glyceryl Oleate | 5.0 | — | — | — |
| Lamesoft ® LMG<br>Glyceryl Laurate (and) Potassium Cocoyl Hydrolyzed Collagen | — | 5.0 | 5.0 | — |
| Gluadin ® WQ<br>Laurdimonium Hydroxypropyl Hydrolyzed Wheat Protein | 3.0 | — | — | — |
| Gluadin ® WK<br>Sodium Cocoyl Hydrolyzed Wheat Protein | — | — | — | — |
| Euperlan ® PK 3000 AM<br>Glycol Distearate (and) Laureth-4 (and) Cocamidopropyl Betaine | 5.0 | 3.0 | 4.0 | — |
| Panthenol | 0.5 | — | — | 0.5 |
| Extract of Example 1 or 2 | 1.0 | 1.0 | 1.0 | 1.0 |
| Arlypon ® F<br>Laureth-2 | 2.6 | 1.6 | — | 1.0 |
| Sodium Chloride | — | — | — | — |

TABLE 15

Cosmetic preparations foam bath (all quantities in % by weight, based on the cosmetic preparation, water, preservative add up to 100% by weight)

| Composition (INCI) | 9 | 10 | 11 | 12 | 13 |
|---|---|---|---|---|---|
| Texapon ® NSO<br>Sodium Laureth Sulfate | — | 30.0 | 30.0 | — | 25.0 |
| Plantacare ® 818<br>Coco Glucosides | — | 10.0 | — | — | 20.0 |
| Plantacare ® PS 10<br>Sodium Laureth Sulfate (and) Coco Glucosides | 22.0 | — | 5.0 | 22.0 | — |
| Dehyton ® PK 45<br>Cocamidopropyl Betaine | 15.0 | 10.0 | 15.0 | 15.0 | 15.0 |
| Monomuls ® 90-O 18<br>Glyceryl Oleate | 0.5 | — | — | — | — |
| Lamesoft ® PO 65<br>Coco-Glucoside (and) Glyceryl Oleate | — | — | 3.0 | 3.0 | 2.0 |
| Cetiol ® HE<br>PEG-7 Glyceryl Cocoate | — | — | — | 2.0 | 2.0 |
| Nutrilan ® I-50<br>Hydrolyzed Collagen | 5.0 | — | — | — | — |
| Gluadin ® W 40<br>Hydrolyzed Wheat Gluten | — | — | 5.0 | 5.0 | — |
| Gluadin ® WK<br>Sodium Cocoyl Hydrolyzed Wheat Protein | — | — | — | — | 7.0 |
| Euperlan ® PK 3000 AM<br>Glycol Distearate (and) Laureth-4 (and) Cocamidopropyl Betaine | 5.0 | — | — | 5.0 | — |
| Arlypon ® F<br>Laureth-2 | — | — | 1.0 | — | — |
| Sodium Chloride | 1.0 | — | 1.0 | — | 2.0 |
| Cassia alata extract of Example 1 or 2 | 1.0 | 1.0 | 1.0 | 1.0 | 1.0 |

TABLE 15

Cosmetic preparations (all quantities in % by weight, based on the cosmetic preparation, water, preservative add up to 100% by weight)

| Composition (INCI) | 14 | 15 | 16 | 17 | 18 | 19 | 20 | 21 | 22 | 23 |
|---|---|---|---|---|---|---|---|---|---|---|
| Dehymuls ® PGPH<br>Polyglyceryl-2 Dipolyhydroxystearate | 4.0 | 3.0 | — | 5.0 | — | — | — | — | — | — |
| Lameform ® TGI<br>Polyglyceryl-3 Diisostearate | 2.0 | 1.0 | — | — | — | — | — | — | — | — |

TABLE 15-continued

Cosmetic preparations (all quantities in % by weight, based on the cosmetic preparation, water, preservative add up to 100% by weight)

| Composition (INCI) | 14 | 15 | 16 | 17 | 18 | 19 | 20 | 21 | 22 | 23 |
|---|---|---|---|---|---|---|---|---|---|---|
| Emulgade ® PL 68/50<br>Cetearyl Glucoside (and) Cetearyl Alcohol | — | — | — | — | 4.0 | — | — | — | 3.0 | — |
| Eumulgin ® B2<br>Ceteareth-20 | — | — | — | — | — | — | — | 2.0 | — | — |
| Tegocare ® PS<br>Polyglyceryl-3 Methylglucose Distearate | — | — | 3.0 | — | — | — | 4.0 | — | — | — |
| Eumulgin VL 75<br>Polyglyceryl-2 Dipolyhydroxystearate (and) Lauryl Glucoside (and) Glycerin | — | — | — | — | — | 3.5 | — | — | 2.5 | — |
| Bees Wax | 3.0 | 2.0 | 5.0 | 2.0 | — | — | — | — | — | — |
| Cutina ® GMS<br>Glyceryl Stearate | — | — | — | — | — | 2.0 | 4.0 | — | — | 4.0 |
| Lanette ® O<br>Cetearyl Alcohol | — | — | 2.0 | — | 2.0 | 4.0 | 2.0 | 4.0 | 4.0 | 1.0 |
| Antaron ® V 216<br>PVP/Hexadecene Copolymer | — | — | — | — | — | 3.0 | — | — | — | 2.0 |
| Myritol ® 818<br>Cocoglycerides | 5.0 | — | 10.0 | — | 8.0 | 6.0 | 6.0 | — | 5.0 | 5.0 |
| Finsolv ® TN<br>C12/15 Alkyl Benzoate | — | 6.0 | — | 2.0 | — | — | 3.0 | — | — | 2.0 |
| Cetiol ® J 600<br>Oleyl Erucate | 7.0 | 4.0 | 3.0 | 5.0 | 4.0 | 3.0 | 3.0 | — | 5.0 | 4.0 |
| Cetiol ® OE<br>Dicaprylyl Ether | 3.0 | — | 6.0 | 8.0 | 6.0 | 5.0 | 4.0 | 3.0 | 4.0 | 6.0 |
| Mineral Oil | — | 4.0 | — | 4.0 | — | 2.0 | — | 1.0 | — | — |
| Cetiol ® PGL<br>Hexadecanol (and) Hexyldecyl Laurate | — | 7.0 | 3.0 | 7.0 | 4.0 | — | — | — | 1.0 | — |
| Panthenol / Bisabolol | 1.2 | 1.2 | 1.2 | 1.2 | 1.2 | 1.2 | 1.2 | 1.2 | 1.2 | 1.2 |
| Cassia alata extract (Example 1 or 2) | 1.0 | 1.0 | 1.0 | 1.0 | 1.0 | 1.0 | 1.0 | 1.0 | 1.0 | 1.0 |
| Copherol ® F 1300<br>Tocopherol/Tocopheryl Acetate | 0.5 | 1.0 | 1.0 | 2.0 | 1.0 | 1.0 | 1.0 | 2.0 | 0.5 | 2.0 |
| Neo Heliopan ® Hydro<br>Sodium Phenylbenzimidazole Sulfonate | 3.0 | — | — | 3.0 | — | — | 2.0 | — | 2.0 | — |
| Neo Heliopan ® 303<br>Octocrylene | — | 5.0 | — | — | — | 4.0 | 5.0 | — | — | 10.0 |
| Neo Heliopan ® BB<br>Benzophenone-3 | 1.5 | — | — | 2.0 | 1.5 | — | — | — | 2.0 | — |
| Neo Heliopan ® E 1000<br>Isoamyl p-Methoxycinnamate | 5.0 | — | 4.0 | — | 2.0 | 2.0 | 4.0 | 10.0 | — | — |
| Neo Heliopan ® AV<br>Octyl Methoxycinnamate | 4.0 | — | 4.0 | 3.0 | 2.0 | 3.0 | 4.0 | — | 10.0 | 2.0 |
| Uvinul ® T 150<br>Octyl Triazone | 2.0 | 4.0 | 3.0 | 1.0 | 1.0 | 1.0 | 4.0 | 3.0 | 3.0 | 3.0 |
| Zinc Oxide | — | 6.0 | 6.0 | — | 4.0 | — | — | — | — | 5.0 |
| Titanium Dioxide | — | — | — | — | — | — | 5.0 | — | — | — |
| Glycerol (86% by weight) | 5.0 | 5.0 | 5.0 | 5.0 | 5.0 | 5.0 | 5.0 | 5.0 | 5.0 | 5.0 |

(14) w/o sun protection cream, (15-17) w/o sun protection lotion, (18,21,23) o/w sun protection lotion, (19,20,22) o/w sun protection cream All substances with the registered trade mark symbol ® listed and used in Tables 12 to 15 are brands and products of the COGNIS Group.

The invention claimed is:

1. An extract of leaves of *Cassia alata* produced by a process comprising heating the leaves in water at 85-90° C. for 1 hour and separating a supernatant liquid extract from insoluble residue, thereby obtaining the extract.

2. The extract of claim 1, wherein the process further comprises spray drying or freeze drying the supernatant liquid extract.

3. The extract of claim 1 which comprises kaempferol-3-O-sophoroside.

4. A skin care composition comprising the extract of claim 1.

5. The skin care composition of claim 4 which comprises 0.001 to 25%, 0.01 to 5%, or 0.05 to 1.5% by weight of the extract.

6. The skin care composition of claim 5 which further comprises 1 to 50% by weight auxiliaries and additives.

7. The skin care composition of claim 4 which is a composition for topical application.

8. The skin care composition of claim 7 which is in the form of a cream or lotion.

9. A method of protecting skin cells from UV-induced damage comprising applying to skin exposed to UV light a skin care composition comprising an extract of leaves of *Cassia alata*, wherein the extract is produced by a process comprising heating the leaves in water at 85-90° C. for 1 hour and separating a supernatant liquid extract from insoluble residue, thereby obtaining the extract.

10. The method of claim 9, wherein wrinkling and/or lining of the skin is reduced.

11. The method of claim 9, wherein apoptosis in the skin cells is reduced.

12. The method of claim 9, wherein inflammation of the skin is reduced.

13. A method of regenerating fibroblasts in skin comprising applying to the skin a composition comprising an extract of leaves of *Cassia alata*, wherein the extract is produced by a process comprising heating the leaves in water at 85-90° C. for 1 hour and separating a supernatant liquid extract from insoluble residue, thereby obtaining the extract, and wherein the composition is applied in an amount sufficient to stimulate glycosaminoglycan synthesis in skin fibroblasts.

14. A method for extracting kaempferol-3-O-sophoroside from leaves of *Cassia alata* comprising heating the leaves in water at 85-90° C. for 1 hour and separating a supernatant liquid extract from insoluble residue, thereby obtaining the extract.

15. The method of claim 14, further comprising spray drying or freeze drying the extract.

* * * * *